(12) United States Patent
Polaschegg

(10) Patent No.: US 6,702,774 B1
(45) Date of Patent: Mar. 9, 2004

(54) METHOD OF MEASURING DIALYSIS OR CLEARANCE OF HEMODIALYSIS SYSTEMS

(75) Inventor: Hans-Dietrich Polaschegg, Koestenberg (AT)

(73) Assignee: Fresenius Medical Care Deutschland GmbH (DE)

( * ) Notice: Subject to any disclaimer, the term of this patent is extended or adjusted under 35 U.S.C. 154(b) by 494 days.

(21) Appl. No.: 09/704,502

(22) Filed: Nov. 2, 2000

Related U.S. Application Data

(63) Continuation of application No. 09/174,375, filed on Oct. 14, 1998, now Pat. No. 6,156,002.

(30) Foreign Application Priority Data

Oct. 27, 1997 (DE) .......................... 197 47 360

(51) Int. Cl.$^7$ ........................... A61M 37/00; C02F 1/44; B01D 11/00; B01D 61/00; G01N 33/20
(52) U.S. Cl. .................... 604/5.01; 604/5.04; 604/6.09; 210/646; 210/647; 210/650; 210/321.71; 210/321.65; 73/61.43; 73/61.48
(58) Field of Search ...................... 604/4.01, 5.01–5.04, 604/6.09; 210/600, 645–47, 85, 321.6, 321.71, 321.65, 739, 745, 929; 600/437–39, 459–68, 481, 504; 73/53.01, 61.41, 61.43, 61.44, 61.48, 866

(56) References Cited

FOREIGN PATENT DOCUMENTS

| DE | 36 40 089 A1 | 6/1988 |
|---|---|---|
| DE | 39 38 662 C2 | 7/1991 |
| EP | 0 547 025 B1 | 6/1993 |
| EP | 0 658 352 B1 | 6/1995 |
| WO | WO 98 32476 A | 7/1998 |

*Primary Examiner*—Patricia Bianco
(74) *Attorney, Agent, or Firm*—Burns & Levinson LLP; Frederick C. Williams; Yan Lan

(57) ABSTRACT

A method for measurement of mass and energy transfer parameters (clearance and dialysance) in hemodialysis. A sensor is provided in the dialysate flow path downstream of the dialyzer and means are provided to add concentrate upstream of the dialyzer. A pre-determined amount of a substance whose dialysance is to be measured is added upstream of the dialyzer. The amount of substance riot dialyzed in the dialyzer is measured downstream of the dialyzer by said sensor by integrating the concentration over time. Dialysance is calculated from the amount added upstream, the amount measured downstream and the dialysate flow. In case the substance is part of the dialysate the base concentration is subtracted during integration. The addition of the concentrate upstream of the dialyzer can be done manually or, alternatively by the mixing pump of the dialysis machine. Instead of an increase of the concentration with a concentrate dilution with water can be used as well.

18 Claims, 3 Drawing Sheets

METHOD OF MEASURING DIALYSIS OR CLEARANCE OF HEMODIALYSIS SYSTEMS

This application is a continuation of application Ser. No. 09/174,375, filed Oct. 14, 1998, now U.S. Pat. No. 6,156,002.

Hemodialysis has developed into a life saving procedure for several hundred thousand patients worldwide. The economic costs have risen dramatically because it is a chronic treatment. To secure treatments for the growing number of patients in the industrial nations and to make treatment possible in emergent countries it is necessary to improve the quality of the method and reduce the costs. Optmization of the method influences costs significantly because a well-treated patient is less morbid and needs less care.

In the USA, the NCDS (National Cooperative Dialysis Study) studied the morbidity of a large patient collective as a function of the dialysis dose. Gotch and Sargent (Kidney International 28, 526–534, 1985) found a simple interpretation for the results: The morbidity decreases from a high value to a low constant one when Kt/V increases from 0.8 to >=1. K is the effective clearance for urea, t is the treatment time and V is the total body water.

The hypothesis that morbidity and mortality are related to Kt/V for urea has been corrobated for the uniform treatment market in the USA but not the interpretation by Sargent and Gotch. New data indicate that the mortality decreases further up to a Kt/V of 1.5. No reliable data are available for greater values because of lack of sufficient patient numbers (See: Parker Thomas F. Short-Time Dialysis Should Be Used Only With Great Caution. Seminars in Dialysis 1993;6:164–167; Hakim R M, Breyer J, Ismail N, Schulman G. Effects of dose of dialysis on morbidity and mortality. Am J Kidney Dis 1994; 23: 670–80 and others).

This understanding has resulted in the development of guidelines in the USA (DOQI guidelines) demanding a minimum dose of Kt/V=1.2 generally and 1.4 for diabetics respectively. These guidelines are now regarded as relevant by the supervising authorities and compliance with these minimum requirements must be demonstrated with the help of appropriate methods.

One possibility is measurement of the effective clearance, the treatment time and the total body water. Measurement of treatment time is trivial, total body water can be measured with known methods, e.g., bioimpedance or with urea kinetic modeling. The effective clearance is difficult to measure with conventional means but in the German patent application DE3938662 the inventor has described a method for in-vitro measurement of the effective electrolyte dialysance that is equal to the effective clearance for urea within the errors of measurement. In-vitro and in-vivo experiments have shown that this method can be performed in practice. Industry advertises this method in conferences, e.g., the EDTA congress in Geneva 1997 and the ASN congress in San Antonio 1997.

The assumption made above that electrolyte dialysance is almost equal to urea dialysance is only correct if the electrolyte is a mixture usually called "acid concentrate" consisting essentially of chlorides. Altering, e.g., the concentration of the total dialysate or the bicarbonate component leads to degradation of agreement.

The method described in DE3938662 calculates the dialysance from the electrolyte transfer measured at two (or more) electrolyte input concentrations. Input and output electrolyte concentrations have to be kept constant over a time period of approximately one to five minutes. Variations result in an error because of the time constant of the measurement. The time constant originates from the filling volume of the dialyzer and results in a delayed and slow settling of the output concentration after a step function on the input. Such a curve is shown in a paper of the inventor: Polaschegg H D, Levin N W. Hemodialysis Machines and Monitors. Jacobs C, Kjellstrand C M, Koch K M, Winchester J F, editors. Replacement of renal function by dialysis, 4th ed. Kluwer academic publishers, 1996:333–79. This book contains all further information regarding the state of the art that is required for the understanding of this description. The variation of the electrolyte concentration is normally done automatically by variation of the mixing ratio between concentrate and water in the dialysis machine. Because the adjustment of a new electrolyte concentration is also subject to a time constant the total measurement takes several minutes and is coupled with a substantial electrolyte transfer that can be compensated subsequently by a controlled addition or subtraction. In general, the method can be used only in newly designed machines. Retrofitting existing machines is laborious and is not offered (by industry). Because of the relatively long measuring time only effective clearance but not dialyzer clearance can be measured with this method. The two values differ by the influence of the recirculation in the blood access and in the circulatory system respectively, a parameter of interest in itself. In any event, the method is only applicable for single patient machines but not for central dialysate supply systems if the modification of the dialysate concentration is done by the mixing system of the dialysis machine. In summary the following disadvantages and limitations apply for the method described (previously) by the inventor that is already in use:

The measurement takes a relatively long time and is related to a non-negligible electrolyte transfer. The method is not applicable to substances not contained in the dialysate (e.g., creatinine, phosphate). The method cannot differentiate between dialyzer clearance and effective clearance.

The goal of this invention is to minimize these disadvantages and in addition to describe a method that can be adapted easily to existing machines without adaptation of the electronic control and that can be used for other substances as well. The method according to the invention is characterized by adding a pre determined amount of a substance to the dialysate circuit upstream of the dialyzer and by measuring the amount of said substance leaving the dialyzer downstream in the dialysate and calculating the dialysance or clearance respectively for the substance added.

The addition of the substance can be done in different ways. Also, a dilution instead of an addition is possible. It is possible to inject a liquid concentrate of a single substance (e.g., NaCl or creatinine) upstream of the dialyzer. Alternatively water only can be injected. Injection can be done manually with a syringe or semiautomatic with a spring operated syringe or automatic with the help of a pump. Also, the concentrate pump of a dialysis machine can be operated at a higher rate for a short period to create an electrolyte bolus. Alternatively to addition of a predetermined amount of a substance a non-predetermined amount can be added that is measured by a sensor arranged upstream of the dialyzer. It is further possible to calibrate a not precisely known but repeatable injectable amount by a first bolus injection with the second injection used for the measurement. The calibration injection is done downstream of the dialyzer but upstream of the sensor or, alternatively, the dialysate circuit is switched into bypass and the calibration injection is done at the same point as the injection for the measurement.

Alternatively to the injection of a liquid substance the addition of an amount of a substance is possible by conveying the dialysate through a powder cartridge or powder bag for a short period.

DESCRIPTION OF PREFERRED EMBODIMENTS

The invention is now described with the help of a mathematical derivation and explained by figures describing various forms of the invention.

Figure 1:
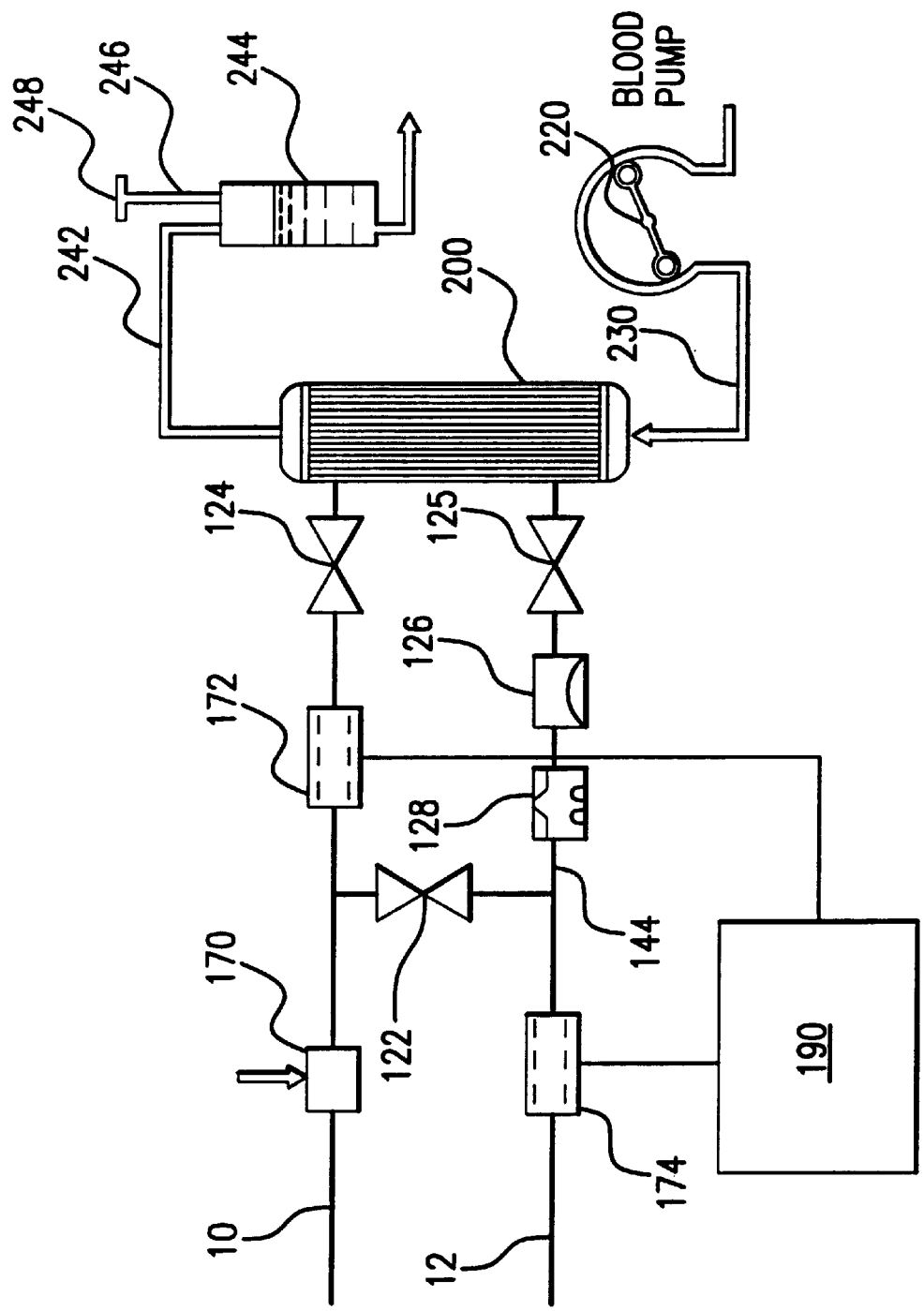
FIG. 1 depicts a portion of the dialysate circuit of atypical dialysis machine.

FIG. 1 shows a section of the dialysate circuit of a conventional dialysis machine. 10 is the conduit that carries dialysate from a dialysate source not shown. The dialysate source can be the mixing system of a single patient machine or alternatively a central dialysate supply system. An injection or addition site 170 is integrated into said conduit through which the amount of substance for the clearance measurement can be added. Following in this conduit is a first optional sensor for the clearance measurement 172 and a first dialyzer valve 124. 200 is the dialyzer separated by a semipermeable membrane into a blood and a dialysate part (not shown). Spent dialysate leaves the dialyzer through conduit 144. It flows through the second dialyzer valve 125, a pressure sensor 126 and a blood leak detector 128 and arrives eventually at the second sensor for clearance measurement 174 and flows subsequently through conduit 12 to waste (not shown). A bypass with bypass valve 122 branches from conduit 10 to conduit 144. The injection site 170 is preferably but not necessarily situated upstream of the bypass valve. The second sensor for clearance measurement is preferably situated downstream of the bypass valve in the waste line. The sensor 174 and the optional sensor 172 are connected to an evaluation unit 190.

Figure 2B:
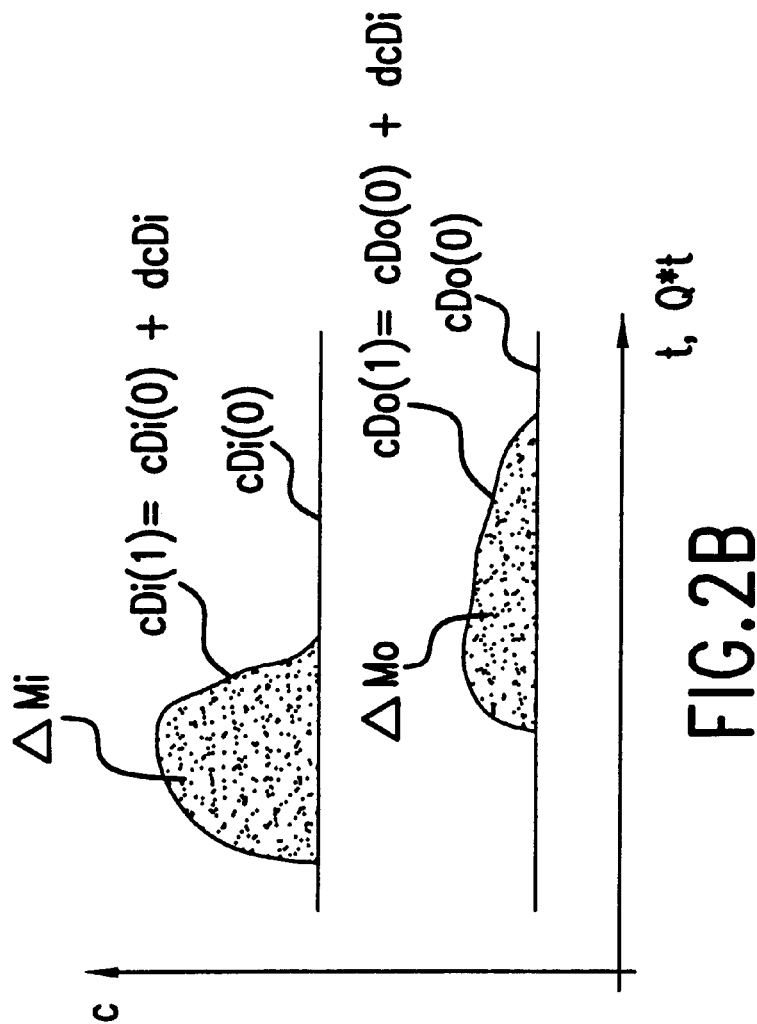
FIG. 2b graphically depicts the quantities used in the method.
Figure 2A:
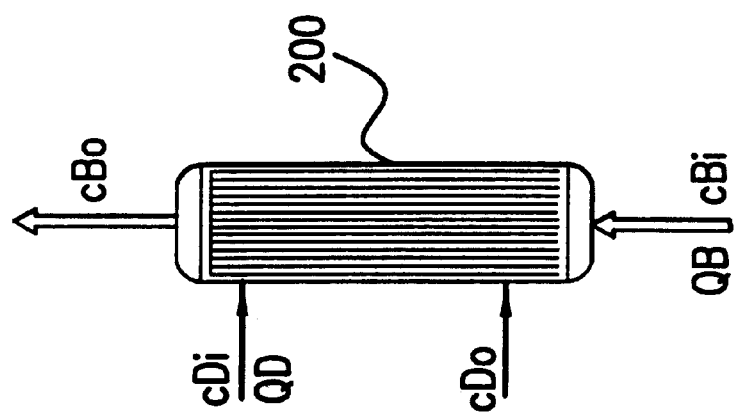
FIG. 2a shows the dialyzer and the notation used in describing the invention.

FIG. 2a shows the dialyzer 200 with the conduits for blood and dialysate leading to and from the dialyzer and the notations used in the mathematical derivation. QB is the blood flow and QD the dialysate flow. cBi is the input blood concentration, cBo the output blood concentration on the blood side of the dialyzer. Dialysate flows on the other side of the membrane, usually in countercurrent mode. cDi is the dialysate input concentration and cDo is the dialysate output concentration.

For the following derivation reference is made to the state of the art as described in mentioned patent DE 3938662 and to the inventor's publication: "Polaschegg H D. Automatic, noninvasive intra dialytic clearance measurement. Int J Artif Organs 1993;16:185–191".

The dialysance D can be calculated from the dialysate flow QD, the dialysate concentrations cDi and cDo and the blood concentration cBi as follows:

$$D = QD * \frac{CDi - CDo}{CBi - CDi} \quad (1)$$

The concentrations before addition of the substance are denoted with the index 0 and the concentration during the substance bolus with the index 1. For the following simplified derivation it is assumed that the dialysate flow and the dialysance (and therefore also the blood flow) are constant during the measurement and that no ultrafiltration takes place. The method according to the invention, however, is also applicable with simultaneous ultrafiltration.
Therefore:

$$D^0 = D^1 = D \text{ And } QD^0 QD^1 = QD \quad (2)$$

A further assumption is made that is correct for the method according to this invention but not for the method described in DE 3938662. It is assumed that the blood input concentration does not change during the measurement.

$$cBi^0 = cBi^1 \quad (3)$$

With (2) and (3), (1) can be converted for both indices as follows:

$$D*CBi - D*cDi^0 = QD*(cDi^0 - cDo^0)$$

$$D*CBi - D*cDi^1 = QD*(cDi^1 - cDo^1) \quad (4)$$

The lower equation of (4) is now used to replace D*cBi in the upper equation. This eliminates the unknown parameter cBi. The result is:

$$D*cDi^1 - cDi^0) = QD*(cDi^1 - cDi^0) - QD*(cDo^1 - cDo^0) \quad (5)$$

And following:

$$D = \frac{QD*(cDi^1 - cDi^0) - QD*(cDo^1 - cDo^0)}{cDi^1 - cDi^0} \quad (6)$$

Both sides are divided by QD:

$$\frac{D}{QD} = \frac{QD*(cDi^1 - cDi^0) - QD*(cDo^1 - cDo^0)}{QD*(cDi^1 - cDi^0)} \quad (7)$$

Assuming that the concentration in the dialysate flowing to the dialyzer does not change, $cDi^1$ can be regarded as the superposition of a constant concentration $cDi^0$ and a bolus concentration dcDi as graphically shown in FIG. 2b.

$$cDi^1 = cDi^0 + dcDi, \; cDo^1 = cdo^0 + dcDo \quad (8)$$

With 7 and 8 it follows:

$$\frac{D}{QD} = \frac{QD*(dcDi) - QD*(dcDo)}{QD*(dcDi)} \quad (9)$$

The integration for dcDi and dcDo respectively over time multiplied by QD is the amount of substance added upstream of the dialyzer and leaving the dialyzer respectively:

$$\Delta M1 = QD * \int dcDi * dt, \; \Delta M2 = QD * \int dcDo * dt \quad (10)$$

The length of the integration interval must be chosen such that the bolus at the outlet decreases to a negligible fraction.

With 9 and 10 follows:

$$D = QD * \frac{\Delta Mi - \Delta Mo}{\Delta Mi} \quad (11)$$

Because the amount of substance $\Delta Mi$ can be predetermined, it is only necessary to measure the concentration at the outlet as function of time and performing an integration after subtraction of the background. In practice this is realized by calculating either continuously a mean value of the outlet concentration or alternatively immediately before the measurement. At the beginning of the addition of the substance the integration program of the evaluation unit 190 is started either automatically or alternatively by an input device not shown. The evaluation unit receives a signal proportional to the dialysate flow from the control unit of the dialysis machine and information about the added amount of substance through a further input device. The constants for the conversion of the sensor signal into a concentration signal are either stored in the evaluation unit or can be programmed through an input unit. Such input units are state of the art and need not be described in detail. Digital and analogue inputs as well as inputs through computers are equally possible.

The evaluation unit now calculates the dialysance D according to equation 11 from the programmed constants and the measured concentration of the substance leaving the dialyzer and displays this on a display or send the information to an external computer or stores it.

It is emphasized that the equations are based on amounts of the substance and concentrations respectively. Usually the concentration of a substance is measured indirectly, e.g., by conductivity. Non-linearity of the relationship between substance concentration or substance amount and the measured parameter must be taken into account. This is, e.g., the case if conductivity is used for measuring and a wide range of conductivity is used. Advantageously the appropriate transfer functions can be stored directly in the evaluation unit 190. Alternatively the signals can be sent directly to a computer. The correction is then done by an appropriate program.

The optional sensor upstream from the dialyzer can be used to measure the amount of substance at the input in case that this is not easily pre-determinable because, e.g., the amount cannot be controlled sufficiently accurately.

Injection of water: In a special variant of the invention water alone is injected. With this method it is no longer possible to measure the dialysance of any substance but only the dialysance of one or more substances contained in fresh dialysate can be measured. The amount of substance $\Delta mi$ at the input is than the volume of the added amount of water. The amount of substance $\Delta mo$ at the outlet is now calculated from the negative bolus relative to the starting concentration. The amount of water injected must be controlled such that the osmolarity of the dialysate does not decrease below the hemolysis limit.

It is possible to remove water for a short period through an appropriate membrane, e.g., reverse osmosis membrane. This case can be treated like an addition of a concentrate.

Interfering effects: The dialysate flow increases for a short period during injection of an amount of substance. Advantageously the point of addition is placed at a distance from the dialyzer such that the bolus reaches the dialyzer only after the flow has normalized. With so called volumetric balancing dialysis systems the injected amount cannot simply remove an equal amount of dialysate to waste because these are closed systems. This amount is backfiltered into the patient or, with ongoing ultrafiltration the ultrafiltration is reduced during the time of the bolus. This may cause a minute disturbance of the starting values which violates the assumptions of 6 and 6 (correctly: equations 2 and 3 on page 6 of the German original). This influence that can be estimated or evaluated experimentally can be programmed as a correction factor in the evaluation unit. Alternatively an equal amount of fluid can be subtracted upstream or downstream of the dialyzer simultaneously to the injection. This can be done manually or automatically with a syringe or a pump or automatically by an increase of the ultrafiltration rate for a short period. Alternatively an expansion chamber or expansion bag can be integrated into the dialysate circuit to avoid pressure spikes caused by the addition.

Assuming that the concentration at maximum is increased by not more than 10% for the measurement of the dialysance of electrolyte solutions, the momentary flow increase is 3 to 5% in case concentrates with 3 to 5 molar concentrations are used. Normally this flow increase can be neglected.

Influence of recirculation: The derivation of the equations assumes a constant concentration at the blood inlet. Accordingly, the dialyzer clearance is measured. The substance added as a bolus is partially transferred to blood and increases the outlet concentration there. This bloodside bolus reaches the blood access. In case of recirculation in this region a part of the bolus will return to the blood inlet side of the dialyzer. If the measurement process is not finished at this point in time, the result is influenced by an increased dialysate bolus at the outlet. The clearance calculated according to 6 (derivation beginning on page 6 of the German text) is reduced compared to the dialyzer clearance. This clearance is called effective clearance. The blood concentration bolus mentioned above travels through the blood circuit of the human and a part of it is recirculated as well and comes back to the blood access after typically 1 to 2 minutes. This recirculation is called cardiopulmonary recirculation. By integrating over a sufficiently long time this influence can be taken into account.

By appropriate design of the volumes in the extracorporeal system and the dialysate circuit and by using short injection boli the contribution of recirculation can be measured not only integrally but also separately, at least approximately.

Figure 3:
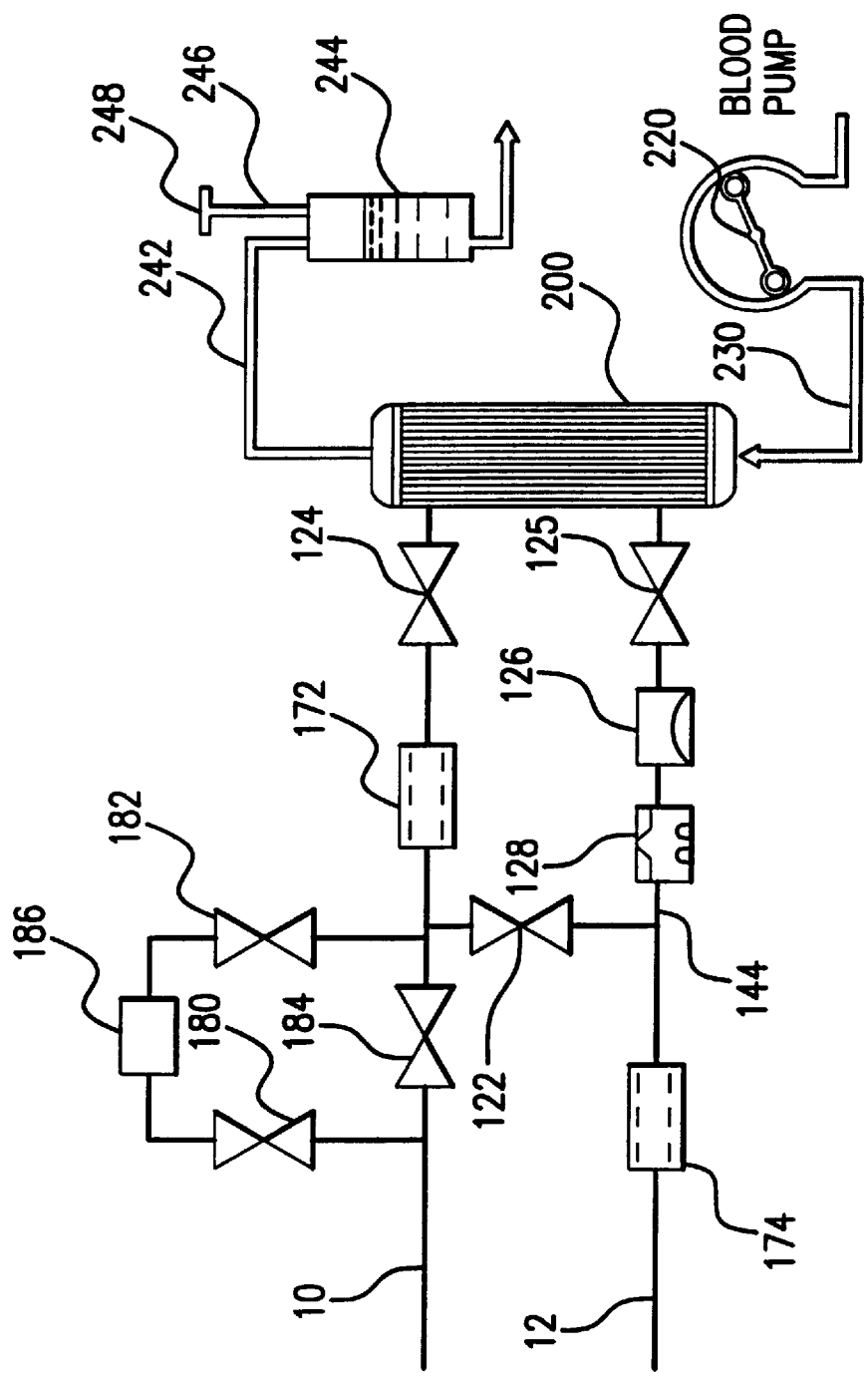
FIG. 3 portrays an alternative embodiment of the arrangement of flows and measurements.

Further embodiments: A further embodiment is shown in FIG. 3. 180, 182 and 184 are valves and 186 is a container containing either liquid or a powdery, granulated, or solid (compressed) concentrate. For the creation of a substance bolus the dialysate flow is guided through the container 186 for a brief period. For this valve 184 is closed and valves 180 and 182 are opened. With this process the dialysate flow is not changed and interferences as described above are avoided. Valve 180 can be designed as a passive spring loaded valve that opens at a defined over pressure, e.g., 0.2 bar. Valve 182 can be designed as passive check valve. When valve 184 is closed the pressure in front of it increases and valve 180 opens. When valve 184 is opened, valve 180 closes again. The container 186 may contain liquid concentrate that is flushed out by the dialysate. The result is a bolus of very short duration. Because the amount is easily controlled by the volume, a sensor upstream of the dialyzer 172 is not required. In case that the container is filled with a solid substance that does not dissolve completely in the dialysate, the dissolved amount is normally not pre determinable. However, it can be measured by the sensor 172. The advantage of this embodiment is that the process can be repeated without refilling of the container. It is, of course, possible to fill the container with a powder that is completely dissolved when dialysate is guided through it. This embodiment is equivalent to filling the container with liquid concentrate.

Sensors: All sensors are applicable that measure the concentration of a substance directly or indirectly and having a sufficient time resolution. For electrolytes a conductivity sensor is advantageous. When a pure substance, e.g., NaCl or NaHCO3 is added upstream the dialysance of this substance can be measured although the conductivity sensor is not specific for this substance. It is, e.g., possible to measure the dialysance for sodium bicarbonate that is lower than the dialysance of urea because of the molecular size, a fact that is usually neglected. When several specific sensors are applied downstream, the dialysance of several substances can be measured simultaneously by adding a mixture of substances upstream. Ion selective electrodes can be used for the measurement of electrolytes.

Optical sensors can be used for the evaluation of the dialysance of non conductive substances. E.g., sensors for optical rotation can be used for the evaluation of the glucose concentration. The dialysance of creatinine and urea and various amino acids can be measured by optical extinction in the ultraviolet region. Normally, the dialysate flow of a dialysis machine is precisely known. If the method according to the invention is used in an add-on device it is advantageous to use a flow sensor and feed its signal to the evaluation unit. In an additional embodiment the signal from the ultrafiltration pump is fed to the evaluation unit and the dialysance can be corrected according to known approximations for the influence of the ultrafiltration.

Calibration: For the calibration of the sensor or, if the added amount of substance is not precisely known, an initial bolus can be injected directly in front of the sensor. This is possible either manually or automatically by opening the bypass valve 122 and simultaneously closing the dialyzer valves 124 and 125. In case the process is controlled automatically by the dialysis machine the dialysate circuit is switched into bypass first and a first bolus is created. Then the bypass is closed again and another bolus is created after the system has stabilized. With this method only good reproducibility but not a precise predetermination of the substance amount or a sensor upstream of the dialyzer is required.

Additional applications: In principle, it is possible to apply the method according to the invention by injecting on the blood side but this is disadvantageous because of the risk of bacterial contamination. The measurement can be done on the dialysate side as described. Measuring on the blood side is normally more difficult because noninvasive sensors have to be used and optical methods are disturbed by hemoglobin and plasma proteins.

The method can be used advantageously in-vitro, for, e.g., quality control. Water can be used on both sides of the membrane and the bolus can be added on the dialysate side or, alternatively on the blood side, because bacterial contamination is not relevant for this measurement. Also, the measurement is possible on both sides. To gain information about the error of the measurement sensors can be applied downstream of both sides. The amount added must then be equal to the sum of the amounts measured on both outlets.

Because a single measurement takes only a few minutes a set of measurements can be done rapidly by injecting single substances either manually or automatically, e.g., a set of all conductive substances including sodium phosphate. A buffered solution can be used instead of water if the dialysance of a weak electrolyte should be measured. The dialysance of acids can be measured with pH sensors.

Heat exchangers: Heat exchangers are described by the same equations as dialyzers. The equations for dialyzers were derived from older equations for heat exchangers. By injecting cold or hot water on one side and measurement of the temperature on the other side it is possible to evaluate the heat transfer coefficient analogue to the evaluation of the dialysance.

Design of the injection site. The equipment for the addition of the amount of substance upstream of the dialyzer can be designed as injection port with a septum or a valve. Also, sampling valves can be used that are opened either manually or automatically when a Luer connector is connected to it.

Amount of substance added: The volume of the solution containing the substance should be as small as possible. Accordingly, the concentration should be as high as possible. The absolute amount of substance is adjusted according to the resolving power of the substance but must not exceed physiological limits. Also, the resulting peak concentrations must not exceed physiological limits positively or negatively. For electrolytes the following estimate applies: The normal electrolyte concentration in the dialysate is approximately 150 mmol/l. Concentrates can be produced up to 5 molar. For a bolus of typically 10% above the normal concentration and a duration of 1 minute an amount of 7.5 mmol is required at a dialysate flow of 500 mL/min. This is equivalent to a volume of 7.5 mmol/5000 mmol/l=1.5 ml. If water is injected injection of 50 ml during 1 minute is required to reduce the concentration by 10%. The injection can be rapid. Because of the non uniform flow in the dialyzer the bolus is dispersed, which reduces the peak concentration.

TABLE 1

Numerical References in Drawings

| Reference-number | Description |
| --- | --- |
| 10 | dialysate inlet conduit from a dialysate source not shown in detail |
| 12 | dialysate conduit for spent dialysate |
| 122 | bypass valve |
| 124 | first dialyzer valve, dialyzer-inlet valve |
| 125 | second dialyzer valve, dialyzer-outlet valve |
| 126 | dialysate pressure sensor |
| 128 | blood leak detector |
| 144 | dialysate outlet conduit, leads from the dialyzer to the waste line 12 |
| 170 | injection site for clearancemeasurement |
| 172 | first sensor for clearancemeasurement |
| 174 | second sensor for clearancemeasurement |
| 180 | first detour valve (elektromagnetic valve or constant pressure valve) |
| 182 | second detour valve (elektromagnetic valve or check valve) |
| 184 | third detour valve (elektromagnetic valve) |
| 186 | cartridge for powder or liquid concentrate |
| 190 | evaluation unit |
| 200 | dialyzer |
| 220 | blood pump |
| 230 | arterial blood tubing set |
| 242 | venous blood tubing set |
| 244 | venous drip chanber |
| 246 | infusion line at the venous drip chamber |
| 248 | connector of the infusion line at the venous drip chamber |
| 312 | flow meter |

I claim:
1. A method of determining mass transfer in hemodialysis or hemodiafiltration using a dialyzer separated into a blood compartment and a dialysate compartment by a semipermeable membrane, said blood compartment comprising part of a fluid circuit connected to a patient or a source of a first liquid and to a discharge, and said dialysate compartment comprising part of a liquid circuit on the dialysate side connected to a source of a second liquid and to a discharge for the second liquid, said liquid circuit further having means for addition into the dialysate upstream of the dialyser a substance of which the mass transfer properties are to be determined, said method comprising the steps of:

adding upstream of the dialyser a bolus of said substance;

measuring over time the concentration of said substance upstream of the dialyser and measuring over time the concentration of said substance downstream of the dialyser and calculating the dialysance from the integral over time of the measured substance concentration minus background concentration over time upstream of the dialyser and from the integral over time of the measured substance concentration minus background concentration over time downstream of the dialyser, and from the flow of liquid through the dialysate compartment.

2. The method of claim 1, wherein the substance is added manually with a syringe.

3. The method of claim 1, wherein a concentrate pump which is an integral part of the dialysis machine performs the addition of said substance.

4. The method of claim 1, wherein the substance is added by detouring the dialysate flow through a container comprising a concentrate.

5. The method of claim 4, wherein the concentrate is a liquid.

6. The method of claim 4, wherein the concentrate is a powder.

7. The method of claim 4, wherein the concentrate is a solid comprising flow channels configured such that the concentrate dissolves only slowly when liquid is conducted therethrough.

8. The method of claim 1, wherein conductivity sensors perform the measuring steps.

9. The method of claim 1, wherein optical sensors perform the measuring steps.

10. The method of claim 9, wherein the optical sensors measure optical-extinction in the ultraviolet region.

11. The method of claim 10, wherein the sensor additionally performs the step of detecting blood leaks.

12. The method of claim 9, wherein a spectrometer is used in the measurement steps.

13. The method of claim 12, wherein a filter spectrometer measures at least two wavelengths.

14. The method of claim 12, wherein the sensor additionally performs the step of detecting blood leaks.

15. The method of claim 9, wherein the sensor additionally performs the step of detecting blood leaks.

16. The method of claim 1, wherein an ion sensitive electrode sensor performs the measuring steps.

17. The method of claim 1, wherein an optical sensor that measures optical rotation or optical refraction is used to perform the measuring steps.

18. The method of claim 1, wherein water is added as a substance upstream of the dialyser.

* * * * *

UNITED STATES PATENT AND TRADEMARK OFFICE
CERTIFICATE OF CORRECTION

PATENT NO. : 6,702,774 B1
DATED : March 9, 2004
INVENTOR(S) : Polaschegg et al.

It is certified that error appears in the above-identified patent and that said Letters Patent is hereby corrected as shown below:

<u>Title page,</u>
Item [75], Inventor, please add the followings:
Helmut Steil, Gelnhausen, Germany Signed and Sealed this Seventh Day of September, 2004

JON W. DUDAS
*Director of the United States Patent and Trademark Office*